(12) United States Patent
Harding et al.

(10) Patent No.: US 7,437,914 B2
(45) Date of Patent: Oct. 21, 2008

(54) MICROFLUIDIC TEST SYSTEMS WITH GAS BUBBLE REDUCTION

(75) Inventors: Philip Harding, Corvallis, OR (US); Christopher C Beatty, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 197 days.

(21) Appl. No.: 11/168,775

(22) Filed: Jun. 28, 2005

(65) Prior Publication Data

US 2006/0288762 A1   Dec. 28, 2006

(51) Int. Cl.
*G01N 35/00* (2006.01)
*G01N 21/00* (2006.01)

(52) U.S. Cl. .................. 73/64.53; 422/50; 422/64; 422/72; 422/100; 436/45

(58) Field of Classification Search ............... 73/64.53; 422/50, 64, 72, 100; 436/45
See application file for complete search history.

(56) References Cited

U.S. PATENT DOCUMENTS

| | | | |
|---|---|---|---|
| 5,242,606 A | 9/1993 | Braynin et al. | |
| 5,256,376 A | 10/1993 | Callan et al. | |
| 5,472,603 A | 12/1995 | Schembri | |
| 5,693,233 A | 12/1997 | Schembri | |
| 6,030,581 A | 2/2000 | Virtanen | |
| 6,063,589 A | 5/2000 | Kellogg et al. | |
| 6,143,248 A | 11/2000 | Kellogg et al. | |
| 6,302,134 B1 | 10/2001 | Kellogg et al. | |
| 6,399,361 B2 | 6/2002 | Brotherston et al. | |
| 6,527,432 B2 | 3/2003 | Kellogg et al. | |
| 6,548,788 B2 | 4/2003 | Kellogg et al. | |
| 6,632,399 B1 | 10/2003 | Kellogg et al. | |
| 6,709,869 B2 | 3/2004 | Mian et al. | |

FOREIGN PATENT DOCUMENTS

| | | |
|---|---|---|
| EP | 0977032 | 2/2000 |
| EP | 1385006 | 1/2004 |
| JP | 55116243 | 9/1980 |
| WO | WO9946045 | 9/1999 |

OTHER PUBLICATIONS

International Search Report for S.N. PCT/US2006/023548 dated Oct. 17, 2006 (6 pages).

*Primary Examiner*—Daniel S. Larkin

(57) ABSTRACT

A reservoir for use in testing a liquid as part of a microfluidic testing system, includes a testing chamber configured to receive the liquid to be tested. A liquid inlet is fluidly coupled to the testing chamber to allow ingress of the liquid into the testing chamber. A gas outlet is fluidly coupled to the testing chamber to allow egress of gas out of the testing chamber. The gas outlet has an elevation that is higher than an elevation of the liquid inlet such that, as the testing chamber is rotated, the gas is expelled out of the testing chamber through the gas outlet, thereby reducing or preventing a presence of gas bubbles in the liquid.

27 Claims, 2 Drawing Sheets

MICROFLUIDIC TEST SYSTEMS WITH GAS BUBBLE REDUCTION

FIELD OF THE INVENTION

The present invention relates generally to systems for manipulating microfluids while minimizing the presence of gas bubbles therein.

BACKGROUND OF THE INVENTION

The use of microfluidic systems for the acquisition of chemical and biological information is becoming increasingly popular due to a number of considerations. For example, complicated biochemical reactions, when conducted in microfluidic volumes, may be carried out using very small volumes of liquid. As the volume of a particular liquid needed for such testing regimes is small, often on the order of nanoliters, the amounts of reagents and analytes used can be greatly reduced. Reduction in the amounts of reagents and analytes can greatly reduce the costs associated with microfluidic testing compared to conventional testing systems.

In addition, the response time of reactions is often much faster in microfluidic systems, leading to a decrease in the overall time required for a particular test regime. Also, when volatile or hazardous materials are used or generated during testing, performing reactions in microfluidic volumes can increase the safety of a testing regime and can also reduce the quantities of hazardous materials that require specialized disposal after testing is completed.

While microfluidic testing is increasing in popularity, the technology associated with microfluidic testing remains problematic in a number of areas. In particular, it has been found that as liquids are centripetally manipulated through various microchannels and chambers formed on or in microfluidic test coupons, gas bubbles can be formed or entrained in the liquids and can interfere with the testing to be performed on the liquids. This interference can take a variety of forms. For example, when liquid is delivered to an optical test chamber to be optically analyzed, the presence of gas bubbles within the liquid can adversely affect the accuracy of the optical test. In addition, when it is desired to chemically react a liquid with a reactant applied to a surface of a testing chamber, the presence of gas bubbles can reduce the interaction between the liquid and the reactant.

Accordingly, while it is desired to use microfluidic test systems in a wide range of applications, the limitations presented by the presence of gas bubbles in microfluidic manipulation of fluids remain problematic.

SUMMARY OF THE INVENTION

It has been recognized that it would be advantageous to develop a system for centripetally manipulating liquids on a microfluidic level while reducing or preventing the presence of gas bubbles in the liquids. The present invention provides a reservoir for use in testing a liquid as part of a microfluidic testing system, including a testing chamber that can be configured to receive the liquid to be tested. A liquid inlet can be fluidly coupled to the testing chamber to allow ingress of the liquid into the testing chamber. A gas outlet can be fluidly coupled to the testing chamber to allow egress of gas out of the testing chamber. The gas outlet can have an elevation that is higher than an elevation of the liquid inlet such that, as the testing chamber is rotated, the gas is expelled out of the testing chamber through the gas outlet, thereby reducing or preventing a presence of gas bubbles in the liquid.

In accordance with another aspect of the invention, a method for reducing or preventing gas bubble presence in a microfluidic liquid to be tested is provided, including the steps of: centripetally manipulating the liquid through a liquid inlet at a first elevation into a testing chamber; and venting a gas through a gas outlet at a second elevation which is higher than the first elevation as the liquid enters the testing chamber.

Additional features and advantages of the invention will be apparent from the detailed description which follows, taken in conjunction with the accompanying drawings, which together illustrate, by way of example, features of the invention.

DETAILED DESCRIPTION OF THE PREFERRED EMBODIMENT(S)

Figure 1:
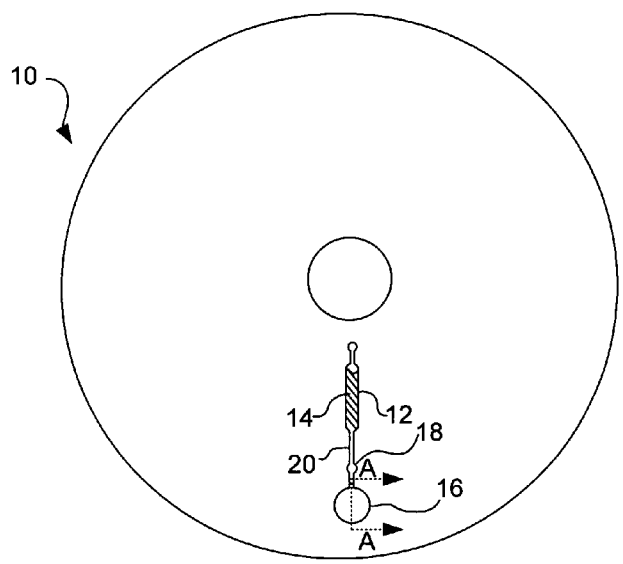
FIG. 1 is a schematic, bottom view of an exemplary microfluidic test coupon incorporating a testing reservoir in accordance with an embodiment of the present invention.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used:

The singular forms "a," "an," and "the" include plural referents unless the context clearly dictates otherwise.

As used herein, the terms "test coupon" or "coupon" are to be understood to refer to a device used to test one or more microfluids in a centrifugation test regime. Test coupons utilized in the present invention can include, but are not limited to, disk-shaped devices formed of poly(methyl methacrylate) ("PMMA"), polystyrene ("PS"), acetonitrile-butadiene-styrene ("ABS"), polycarbonate, etc. While not so limited, such disks can be similar in appearance to well-known compact disks ("CDs").

As used herein, the term "passive valve" is to be understood to refer to a static valve with no moving parts that acts as a fluid valve due primarily to its geometric configuration.

As used herein, the term "capillary valve" is to be understood to refer to a passive valve presenting a junction between two or more capillary channels and/or reservoirs having at least one dimension less than about 1 mm.

As used herein, the term "microfluidics" and "microfluid" are to be understood to refer to fluids manipulated in systems that confine the fluids within geometric channels, passages or reservoirs having at least one dimension less than about 1 mm. Similarly, the terms "microfluidic channel," or "microchannel" are to be understood to refer to channels having at least one dimension less than about 1 mm.

It is to be understood that the various features shown in the attached figures are for the purposes of illustration and do not in any manner limit the present invention. In particular, various fluids may be represented in the figures by hatch lines. The hatch lines used to indicate the presence of a fluid are not to be construed to limit the invention to any particular type of fluid or material, even in the case where the hatch lines used may correspond to hatch lines used by those in various fields of endeavor to indicate a specific fluid or material.

The various microchannels and reservoirs utilized in the present centrifugation coupons can be formed in the coupon in a variety of manners. In one embodiment, these features can be machined in a surface of a disk using conventional milling techniques. After milling, a covering, such as a thin polymer film, can be applied over each channel and/or reservoir to enclose the respective channel and/or reservoir. In addition to this method, it is contemplated that the geometric features of the test coupons can be formed in a variety of manners known to those having ordinary skill in the art, including, for example, injection molding techniques.

In addition, the relative levels of fluids in various reservoirs are shown schematically herein to aid in understanding of the invention, and may not provide an accurate indication of an actual amount of fluid or liquid contained within a reservoir or channel. Also, it is to be understood that liquids contained within channels, reservoirs or chambers can be forced toward one side or another of the channel, reservoir, or chamber, depending upon the net forces acting on the fluid body due to gravity, centripetal force, etc. Therefore, the fact that a body of fluid is shown in the figures as having an "upper" surface oriented in any particular direction may not correspond to the actual orientation of a fluid in a channel, reservoir, or chamber.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention provides systems for manipulating liquids on a microfluidic level while minimizing or eliminating gas bubble presence in the liquids. The present invention can be used to improve manufacturing and testing processes, and other related processes, that are executed on a microfluidic level. Examples of testing processes that can benefit from the present invention include microfluidic biological, enzymatic, immunological and chemical assay regimes. It has been desirable to perform such testing on a microfluidic level for several reasons. Among other reasons, such systems generally utilize volumes of testing fluids well below those used in conventional systems, leading to advantages in decreased costs, more rapid reaction times and minimized production and/or use of biohazardous materials.

Before explaining in detail the features of the reservoirs or testing chambers and systems provided by the present invention, FIG. 1 illustrates generally a microfluidic test coupon 10 with which the testing chambers of the present invention can be incorporated. While not so required, the test coupon can have a diameter on the order of about eight (8) cm and can have a thickness (T, in FIG. 1A) on the order of about five (5) mm. In one embodiment of the invention, the test coupon has a diameter on the order of about twelve (12) cm and a thickness less than about two (2) mm. Such test coupons have been utilized in a number of conventional microfluidic test systems.

Figure 1A:
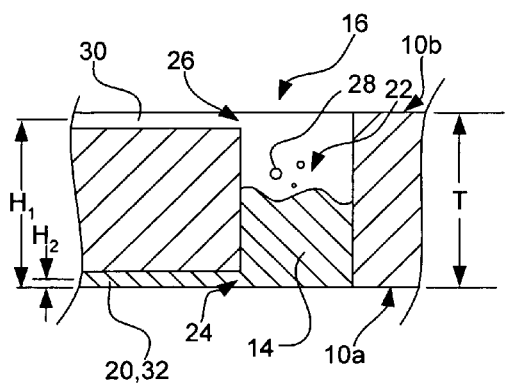
FIG. 1A is an inverted, edgewise cross sectional view of the testing chamber of the microfluidic test coupon of FIG. 1, as viewed along section A-A of FIG. 1.
Figure 1B:
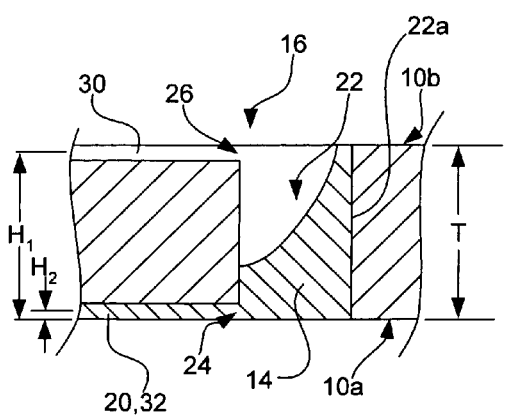
FIG. 1B is an inverted, edgewise cross sectional view of the testing chamber of FIG. 1A, shown during rotation of the test coupon.
Figure 2:
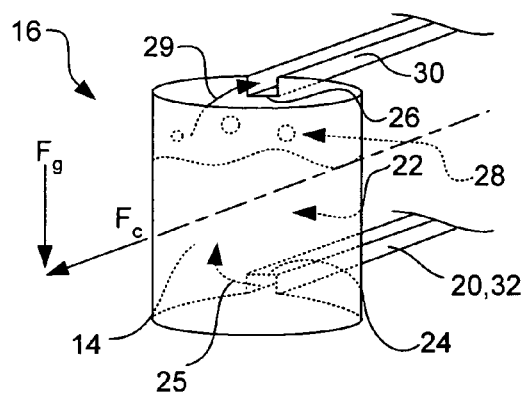
FIG. 2 is a partial, perspective view of the microfluidic testing reservoir of FIGS. 1-1B.

The test coupon 10 can include a fluid receptacle 12 that can contain a liquid 14 and that can be fluidly coupled to a reservoir 16 that can include a liquid testing chamber (22 in FIGS. 1A, 1B and 2). The testing chamber 22 can form a part of, or substantially all of, the fluid reservoir 16. A microchannel 20 can fluidly connect the fluid receptacle to the reservoir. A passive valve 18, which can be a capillary valve, can be fluidly disposed inline with the microchannel 20 and can be utilized to control flow of the liquid 14 from the receptacle 12 to the mixing chamber 16 of the fluid reservoir. In use, the liquid can be held within the receptacle until the coupon is rotated at a particular rate, at which time the capillary valve is designed to release the liquid to allow the liquid to flow into the test chamber. Once delivered to the test chamber, the liquid can be subject to chemical, optical, or other testing regimes; or to various treatments that may be beneficial in manufacturing endeavors.

The various microchannels and reservoirs utilized in the present test coupons can be formed in the coupon in a variety of manners. In one embodiment, these features can be machined in an upper or lower surface of a disk using conventional milling techniques. After milling, a covering, such as a thin polymer film (not shown in the figures), can be applied over each channel and reservoir to enclose each channel or reservoir. In addition to this method, it is contemplated that the geometric features of the test coupons can be formed in a variety of manners known to those having ordinary skill in the art.

The passive valve or capillary valve 18 can be configured to allow flow of the liquid 14 from the fluid receptacle 12 when the coupon 10 rotates at or above a particular, target rotational velocity. Such passive valves have been found advantageous due to their relative simplistic operation and generally require no moving parts or control circuitry to open or close the valves.

The passive, capillary valves utilized in embodiments of the present invention are based on the use of rotationally-induced fluid pressure which, when exceeding a particular pressure, is sufficient to overcome capillary forces which tend to prevent liquids from flowing. Liquids which completely or partially wet internal surfaces of microchannels which contain them experience a resistance to flow when moving from a microchannel of narrow cross section to one of larger cross section. Conversely, liquids that do not wet these surfaces resist flowing from microchannels of large cross section to those with smaller cross section. The capillary pressure can vary according to the sizes of the two microchannels in question, the surface tension of the fluid, and the contact angle of the fluid on the material of the microchannels.

The size of microchannels utilized in the present invention is generally less than about 1 mm, and often as small as about 500 μm or less. By varying capillary valve cross sectional dimensions, as well as the position and extent along the radial direction of the fluid flow components of various test coupons, capillary valves are developed which release fluid flow in a rotation-dependent manner. Capillary valve systems similar to those utilized herein are discussed in detail in publications such as U.S. Pat. No. 6,143,248.

In one embodiment of the invention, the reservoir 16 can be used in testing the liquid 14 as part of a microfluidic testing system. Shown in more detail in FIGS. 1A and 2, the reservoir can include a primary testing chamber 22 configured to receive the liquid to be tested. A liquid inlet 24 can be fluidly coupled to the testing chamber to allow ingress of the liquid (shown schematically by directional reference 25 in FIG. 2) into the testing chamber. A gas outlet 26 can be fluidly coupled to the testing chamber to allow egress of gas (shown schematically by gas bubbles 28 in FIG. 1A) out of the testing chamber. The egress of the gas 28 is shown schematically by directional reference 29 in FIG. 2.

The gas outlet 26 can have an elevation ($H_1$ in FIG. 1A) that is higher than an elevation ($H_2$ in FIG. 1A) of the liquid inlet 24. In this manner, as the liquid 14 enters the testing chamber 22 through the liquid inlet, the gas 28 is expelled out of the testing chamber through the gas outlet. By orienting the liquid inlet and gas outlet with different elevations, the present invention reduces or prevents the formation of gas bubbles after the liquid has entered the testing chamber. By reducing or preventing the presence of gas bubbles in the testing chamber, the integrity and accuracy of testing performed on the liquid can be greatly improved.

For purposes of clarification of the invention, the elevation $H_2$ of the liquid inlet 24 and the elevation $H_1$ of the gas outlet 26 are shown referenced in FIG. 1A as measured from a lowermost surface 10a of disk 10. It is to be understood, however, that, as used herein, the term "elevation" is used to refer to a relative elevation between two or more objects, with reference to a "higher" elevation being understood to mean higher relative to the gravitational vector ($F_g$ in FIG. 2). The force of gravity can, depending upon the rotational rate at which the disk is rotated, contribute to the behavior of liquids in systems such as those discussed herein. As a result, relative elevation of two or more parts of the system, with reference to the vertical gravitational vector, is at times, relevant when examining the behavior of gas bubbles. Thus, in the embodiment shown, gas bubbles formed in, or present in, the liquid 14 can be forced upwardly with respect to the gravitational vector as the force of gravity compels the liquid downwardly with respect to the gravitational vector.

In addition to the gravitational force, or in some cases to the exclusion of the gravitational force, the present invention can utilize centripetal force to prevent or reduce the presence of gas bubbles 28 in the liquid 14. As shown in FIG. 2, as the test coupon (not shown in FIG. 2) incorporating testing chamber 22 is rotated, in either a counterclockwise or clockwise direction, centripetal forces are developed that act on the liquid in the direction shown by $F_c$. These centripetal forces are in addition to the force of gravity shown at $F_g$ and are often much larger in magnitude than the force of gravity. The result of the two forces acting on the liquid, as the testing chamber is rotated, is that any potential gas bubbles 28 (28 in FIG. 1A) that may be formed, or are already present, in the liquid as it enters the testing chamber are forced upwardly and radially inwardly, and are subsequently vented through gas outlet 26, as shown by direction indicator 29 in FIG. 2.

While the gas outlet 26 is discussed herein as part of a path through which gas bubbles are allowed to vent from the testing chamber 22, it is to be understood that the gas outlet can also be utilized to drain liquid 14 from the testing chamber. For example, after testing has been performed on the liquid, it can be drained or vented through the gas outlet to a waste reservoir (not shown) or another location on the disk 10. Thus, the gas outlet is not limited to providing a path for the flow of only gas.

FIG. 1B illustrates a sample configuration in which the liquid 14 has been subject to centrifugal forces induced by rotation of the test coupon 10. As will be appreciated by those of ordinary skill in the art, as the centripetal forces acting on the fluid overcome the force of gravity acting downward on the fluid, the liquid becomes "pinned" against an outer wall 22a of the testing chamber 22. In the extreme case (not shown), the liquid can be pinned against the outer wall of the chamber in a nearly vertical orientation. Thus, as the rotational velocity of the disk increases, the centripetal forces increasingly dominate the net forces on the liquid and the liquid is compelled toward the outer wall in spite of the gravitational force acting downward on the liquid.

The liquid inlet 24 and the gas outlet 26 can be formed in or on the test coupon 10 in a variety of configurations. In the embodiment illustrated in FIG. 1A, the gas outlet can be formed in an uppermost section of the testing chamber, flush with an upper surface 10b of the test coupon. The liquid inlet can be formed in a lowermost section of the testing chamber, flush with a lower surface 10a of the test coupon. In this manner, the liquid inlet and the gas outlet can be formed using conventional milling techniques (performed on opposing sides or surfaces of the disk), without requiring that internal sections of the disk be machined. In addition, an outlet microchannel 30 can be fluidly coupled to the gas outlet 26 of the testing chamber 16. An inlet microchannel 32 can be fluidly coupled to the liquid inlet 24 of the testing chamber. In one embodiment, the outlet microchannel and inlet microchannel can each be at least partially aligned with a radial axis of the test coupon (e.g., an axis extending radially outward from a center of rotation of the test coupon) on or in which the testing chamber is disposed.

The testing chamber 22 can be configured such that a variety of tests can be performed upon the liquid 14 when contained within the chamber. For example, in one embodiment, the testing chamber can be at least partially transparent, to facilitate performance of an optical test on the liquid. In one aspect of the invention, at least a portion of an inside surface of the testing chamber can be treated with a reactant configured to chemically react with the liquid upon entry of the liquid into the testing chamber. While the shape and size of the testing chamber can also vary, in one embodiment of the invention the testing chamber is substantially cylindrical in shape. In a wide array of types of testing that can be performed on the liquid, the reduction or elimination of gas bubble presence in the liquid will enhance the testing process.

It is to be understood that the exemplary test coupon 10 shown in FIG. 1 can contain various other fluid receptacles, microchannels, reservoirs and testing chambers, depending on the configuration required for a particular testing regime. For example, while only microchannel 20 is shown delivering liquid to testing reservoir 16, the present invention can be modified such that two or more microchannels each deliver a different liquid to the reservoir, and accordingly, to the testing chamber 22 of the reservoir. Also, the present invention may be modified such that liquid 14 travels through other testing chambers prior to being received by testing chamber 22. The present invention can thus be incorporated into testing regimes that require various flow sequencing events, with various liquids traveling through portions of the disk at varying times.

In use, the present invention also provides a method for reducing or preventing gas bubble presence in the microfluidic liquid 14 which is to be tested. With reference to FIG. 1A, the method can include the step of centripetally manipulating the liquid through the liquid inlet 24 at the first elevation $H_2$ into the testing chamber 16. The method can also include the step of venting the gas 28 through the gas outlet 26 at the second elevation $H_1$, which can be higher than the first elevation, as the liquid enters the testing chamber. While the order in which the various steps taken to test the liquid can vary, in one aspect of the invention, the step of centripetally manipulating the liquid and the step of venting the gas can be performed substantially simultaneously.

The present invention also provides a method for forming the microfluidic testing chamber 22 that reduces or eliminates presence of gas bubbles 28 in the liquid 14 entering thereinto. The method can include the step of attaching the inlet microchannel 32 to the liquid inlet 24 of the testing chamber at a first elevation $H_2$ to fluidly connect the testing chamber to a microfluidic system (not shown) and to allow introduction of the liquid into the testing chamber. The method can include the step of attaching a gas outlet 26 to the testing chamber at a second elevation $H_1$ higher than the first elevation of the liquid inlet such that, as the liquid enters the testing chamber through the liquid inlet, gas is expelled out of the testing chamber through the gas outlet.

Figure 3:
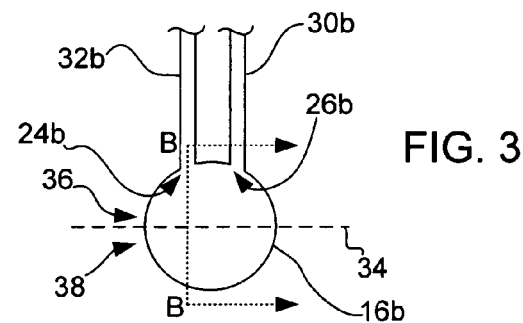
FIG. 3 is a schematic top, sectional view of a testing reservoir in accordance with another embodiment of the invention.
Figure 3B:
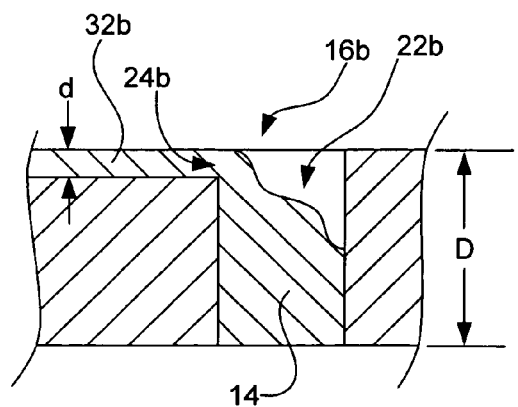
FIG. 3B is an edgewise, cross sectional view of the testing chamber of FIG. 3, as viewed along section B-B of FIG. 3.

Turning to FIGS. 3 and 3B, in one embodiment of the invention a reservoir 16b is provided for use in testing a liquid (14 in FIG. 3B) as part of a microfluidic testing system. The reservoir can include a testing chamber 22b configured to receive the liquid to be tested. A liquid inlet 24b can be fluidly coupled to the testing chamber to allow ingress of the liquid into the testing chamber via inlet microchannel 32b. A gas outlet 26b (not shown in FIG. 3B) can be fluidly coupled to the testing chamber to allow egress of gas out of the testing chamber via outlet microchannel 30b. It is noted that the orientation of the liquid 14 in FIG. 3B is shown under minimal centrifugal force; with the liquid simply filling the chamber 22b from the liquid inlet 24b.

The testing chamber can have a depth "D" that is at least three times a depth "d" of the liquid inlet. As in other embodiments discussed herein, as the liquid 14 enters the testing chamber 22b through the liquid inlet 24b the gas is expelled out of the testing chamber through the gas outlet 26b to thereby reduce or prevent the presence of gas bubbles in the liquid as it enters the testing chamber.

The depth "d" of the liquid inlet 24b and the depth "D" of the testing chamber 22b can vary, as can the ratio of one to another. In one embodiment, the depth of the liquid inlet can range from about 100 µm to about 1000 µm. The depth of the testing chamber can range from about 2 mm to about 10 mm. In one aspect of the invention, the depth of the liquid inlet is about 500 µm and the depth of the testing chamber is about 5 mm. In one embodiment, the depth of the testing chamber is at least four times a depth of the liquid inlet. Thus, in general, the testing chamber will have a depth substantially larger than a depth of the liquid inlet.

As shown in FIG. 3, in one embodiment of the invention, the liquid inlet 24b and the gas outlet 26b can each be fluidly coupled to the reservoir 16b or testing chamber 22b (not shown in FIG. 3) on a radially inward side of the testing chamber. This relationship is illustrated by demarcation 34 which indicates the division of reservoir 16b into two halves: a radially inward half 36 and a radially outward half 38. By forming the liquid inlet and the gas outlet in the radially inward half 36 of the chamber (or coupling them to the radially inward half), centrifugal forces acting on the liquid 14 in the testing chamber 22b cause the liquid to be pinned against the radially outwardmost wall of the chamber and allow the gas to exit the chamber through the radially inwardmost wall of the chamber.

The test coupon 10 discussed herein is provided as an example of a system within which the present invention can be incorporated and is generally designed to be rotated to manipulate the microfluids discussed herein. The mechanism used to rotate or spin test coupons utilized by the present invention is not shown in the figures: it being understood that those having ordinary skill in the art can devise numerous rotational devices capable of rotating the present test coupons at rotational velocities suitable for the present methods.

In addition, while it is anticipated that the present invention can be utilized in a variety of testing regimes, no specific testing regime is detailed herein, as it is believed that those of ordinary skill in the art can readily incorporate the present invention into a variety of testing regimes. In particular, it is contemplated that the present invention can be advantageously incorporated into testing regimes that utilize multiple fluid reservoirs, testing chambers, microchannels, reagents, etc., to perform multiple stages of tests and multiple flow sequencing events, as would occur to one having ordinary skill in the art. It is contemplated that the present invention can be particularly effective in reducing or preventing the presence of bubbles when two or more fluids are sequentially introduced into a single testing chamber.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A device for use in testing a liquid in a microfluidic testing system, comprising:
    a disk defining an axis of rotation and configured to centripetally manipulate the liquid as the disk is rotated about the axis of rotation, the disk including:
        a testing chamber configured to receive the liquid to be tested,
        a liquid inlet fluidly coupled to the testing chamber to allow ingress of the liquid into the testing chamber, and
        a gas outlet fluidly coupled to the testing chamber to allow egress of gas out of the testing chamber,
    wherein the gas outlet has an elevation that is higher than an elevation of the liquid inlet such that, as the disk is rotated about the axis of rotation, gas is expelled out of the testing chamber through the gas outlet, thereby reducing a presence of gas bubbles in the test chamber,
    wherein the gas outlet is formed in an uppermost section of the testing chamber, and wherein the liquid inlet is formed in a lowermost section of the testing chamber.

2. The device of claim 1, wherein the disk has a thickness less than about 2 mm.

3. The device of claim 1, further comprising an outlet microchannel fluidly coupled to the gas outlet of the testing chamber, and an inlet microchannel fluidly coupled to the liquid inlet of the testing chamber, the outlet microchannel and inlet microchannel each being at least partially aligned with a radial axis of the disk.

4. The device of claim 1, wherein the testing chamber is at least partially transparent, to facilitate performance of an optical test on the liquid.

5. The device of claim 1, wherein at least a portion of an inside surface of the testing chamber is treated with a reactant configured to chemically react with the liquid upon entry of the liquid into the testing chamber.

6. The device of claim 1, wherein the testing chamber is substantially cylindrical in shape.

7. A method for forming a device for use in testing a liquid in a microfluidic testing system, the device including a disk defining an axis of rotation and configured to centripetally manipulate the liquid as the disk is rotated about the axis of rotation, the disk including a microfluidic testing chamber that reduces or eliminates the formation or presence of gas bubbles in a liquid entering thereinto, the method comprising the steps of:

coupling a liquid inlet fluidly to the testing chamber, such that, as the disk is rotated about the axis of rotation, the liquid is driven centripetally into the testing chamber; and coupling a gas outlet to the testing chamber on a radially inward side of the testing chamber such that, as the disk is rotated about the axis of rotation, gas is expelled out of the testing chamber through the gas outlet on the radially inward side of the testing chamber, wherein the gas outlet is formed in an uppermost section of the testing chamber and wherein the liquid inlet is formed in a lowermost section of the testing chamber.

8. The method of claim 7, wherein the disk has a thickness of less than about 2 mm.

9. The method of claim 7, comprising the further step of fluidly coupling an inlet microchannel to the liquid inlet and an outlet microchannel to the gas outlet of the testing chamber such that the outlet microchannel and the inlet microchannel are each at least partially aligned with a radial axis of the disk.

10. The method of claim 7, wherein the testing chamber is at least partially transparent, to facilitate performance of an optical test on the liquid.

11. The method of claim 7, wherein at least a portion of an inside surface of the testing chamber is treated with a reactant configured to mix with the liquid upon entry of the liquid in the testing chamber.

12. The method of claim 7, wherein the testing chamber is substantially cylindrical in shape.

13. A device for use in testing a liquid in a microfluidic system, comprising:

a disk defining an axis of rotation and configured to centripetally manipulate the liquid as the disk is rotated about the axis of rotation, the disk including:

a testing chamber configured to receive the liquid to be tested, a liquid inlet fluidly coupled to the testing chamber to allow ingress of the liquid into the testing chamber when the disk is rotated, and a gas outlet fluidly coupled to the testing chamber to allow egress of gas out of the chamber, wherein the gas outlet couples to the testing chamber on a radially inward side of the testing chamber such that, as the disk is rotated, gas is expelled out of the testing chamber through the gas outlet, thereby reducing a presence of gas bubbles in the testing chamber, wherein the gas outlet is formed in an uppermost section of the testing chamber, and wherein the liquid inlet is formed in a lowermost section of the testing chamber.

14. A method for reducing or preventing presence of gas bubbles in a liquid to be tested using the device of claim 13, comprising the steps of:

rotating the disk about the axis of rotation such that the liquid is centripetally driven through the liquid inlet into the testing chamber; and venting gas through the gas outlet as the liquid enters the testing chamber.

15. The method of claim 14, wherein the step of rotating the disk and the step of venting gas are performed substantially simultaneously.

16. The method of claim 14, wherein the disk has a thickness less than about 2 mm.

17. The method of claim 14, further comprising an outlet microchannel fluidly coupled to the gas outlet of the testing chamber, and an inlet microchannel fluidly coupled to the liquid inlet of the testing chamber, the outlet microchannel and the inlet microchannel each being at least partially aligned with a radial axis of the disk.

18. The method of claim 14, further comprising a step of performing an optical test on the liquid.

19. The method of claim 14, wherein at least a portion of an inside surface of the testing chamber is treated with a reactant, and wherein the method further comprises a step of chemically reacting the reactant with the liquid in the testing chamber.

20. The device of claim 13, wherein the disk includes a fluid receptacle fluidly coupled to the testing chamber and disposed radially inward from the testing chamber such that liquid in the fluid receptacle is urged to the testing chamber when the disk is rotated about the axis of rotation.

21. The device of claim 13, wherein both the liquid inlet and the gas outlet are disposed on a radially inward side of the testing chamber.

22. The device of claim 13, wherein the gas outlet and the liquid inlet each couples to the testing chamber at a respective elevation, and wherein the elevation of the gas outlet is higher than the elevation of the liquid inlet.

23. The device of claim 13, further comprising an outlet microchannel fluidly coupled to the gas outlet of the testing chamber and an inlet microchannel fluidly coupled to the liquid inlet of the testing chamber, the outlet microchannel and the inlet microchannel each being at least partially aligned with a radial axis of the disk.

24. The device of claim 23, wherein the outlet microchannel is disposed above the inlet microchannel.

25. The device of claim 13, wherein at least a portion of an inside surface of the testing chamber is treated with a reactant configured to chemically react with the liquid upon entry of the liquid into the testing chamber.

26. The device of claim 13, where the testing chamber is substantially cylindrical in shape.

27. A device for use in testing a liquid in a microfluidic system, comprising:

a disk defining an axis of rotation and configured to centripetally manipulate the liquid as the disk is rotated about the axis of rotation, the disk including:

a testing chamber configured to receive the liquid to be tested, a liquid inlet fluidly coupled to the testing chamber to allow ingress of the liquid into the testing chamber when the disk is rotated, a gas outlet fluidly coupled to the testing chamber to allow egress of gas out of the chamber, an inlet microchannel fluidly coupled to the liquid inlet of the testing chamber, and an outlet microchannel fluidly coupled to the gas outlet of the testing chamber, wherein the gas outlet couples to the testing chamber on a radially inward side of the testing chamber such that, as the disk is rotated, gas is expelled out of the testing chamber through the gas outlet, thereby reducing a presence of gas bubbles in the testing chamber, wherein the outlet microchannel and the inlet microchannel are each at least partially aligned with a radial axis of the disk, and wherein the outlet microchannel is disposed above the inlet microchannel.

* * * * *